United States Patent [19]
Dung et al.

[11] Patent Number: 5,286,401
[45] Date of Patent: Feb. 15, 1994

[54] USE OF HETEROCYCLIC COMPOUNDS AS BLEACH ACTIVATORS OR OPTICAL BRIGHTENERS IN WASHING AND CLEANING AGENTS

[75] Inventors: Bernhard Dung, Gruenstadt; Wolfgang Trieselt, Ludwigshafen; Erwin Hahn, Heidelberg; Johannes Perner, Neustadt; Alfred Oftring, Bad Duerkheim, all of Fed. Rep. of Germany

[73] Assignee: BASF Aktiengesellschaft, Ludwigshafen, Fed. Rep. of Germany

[21] Appl. No.: 836,279

[22] PCT Filed: Nov. 13, 1990

[86] PCT No.: PCT/EP90/01897

§ 371 Date: Mar. 3, 1992

§ 102(e) Date: Mar. 3, 1992

[87] PCT Pub. No.: WO91/08279

PCT Pub. Date: Jun. 13, 1991

[30] Foreign Application Priority Data

Nov. 21, 1989 [DE] Fed. Rep. of Germany ....... 3938526

[51] Int. Cl.$^5$ .................... C07D 265/22; C11D 3/395; D06L 3/02; D06L 3/12
[52] U.S. Cl. ........................................ 252/102; 8/111; 252/98; 252/99; 252/186.4; 252/301.26; 252/524; 252/543; 544/92; 562/2
[58] Field of Search ................ 252/98, 102, 524, 543, 252/186.4; 544/92; 562/2; 8/111

[56] References Cited

U.S. PATENT DOCUMENTS 3,822,114  7/1974  Montgomery ........................ 8/111
4,966,723 10/1990  Hodge ................. 252/102

FOREIGN PATENT DOCUMENTS 099197  6/1983  European Pat. Off. .
0240057 3/1987  European Pat. Off. .
0314350 5/1989  European Pat. Off. .
0332294 9/1989  European Pat. Off. .
1392448 2/1965  France .
1513274 2/1968  France .

OTHER PUBLICATIONS

Journal Organism Chemical, vol. 14, David T. Zentmyer, et al. "The So-Called Acylanthranils (3,1,4-benzoxazones). I. Preparation; Reactions with Water, Ammonia, and Aniline; Structure", pp. 367-381 (1949).

Primary Examiner—Dennis Albrecht
Attorney, Agent, or Firm—Oblon, Spivak, McClelland, Maier & Neustadt

[57] ABSTRACT

Heterocyclic compounds which are useful as bleach activators or optical brighteners in washing and cleaning agents have the formula

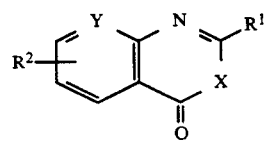

where the variables have the following meanings:
X is O, S or the group N—R$^3$, where R$^3$ is hydrogen, C$_1$-C$_{25}$-alkyl, C$_1$-C$_{25}$-acyl or an aryl group of up to 12 carbon atoms,
Y is CH or N,
R$^1$ for X=S or N—R$^3$ is hydrogen, a C$_1$-C$_{25}$-alkyl or C$_2$-C$_{25}$-alkenyl group or a phenyl radical which may be additionally substituted by one or two C$_1$-C$_4$-alkyl, C$_1$-C$_4$-alkoxy, hydroxyl, carboxyl, sulfo, amino, C$_1$-C$_4$-acylamino, nitro or cyano groups or chlorine or bromine atoms, which substituents, if there are two of them, may be identical or different,
R$^1$ for X=O is phenyl, o-, m- or p-tolyl, p-chlorophenyl, m-nitrophenyl, m-methoxyphenyl or m-methylsulfonylphenyl,
R$^2$ for X=S or N—R$^3$ is hydrogen, a C$_1$-C$_4$-alkyl, C$_1$-C$_4$-alkoxy, hydroxyl, carboxyl, sulfo, amino or C$_1$-C$_4$-acylamino group or a chlorine or bromine atom, and
R$^2$ for X=O is hydrogen.

5 Claims, No Drawings

USE OF HETEROCYCLIC COMPOUNDS AS BLEACH ACTIVATORS OR OPTICAL BRIGHTENERS IN WASHING AND CLEANING AGENTS

The present invention relates to the use of heterocyclic compounds of the general formula I

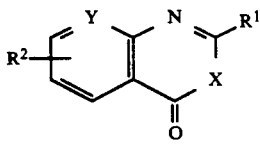

where the variables have the following meanings:

X is O, S or the group N—$R^3$, where $R^3$ hydrogen, $C_1$–$C_{25}$-alkyll $C_1$–$C_{25}$-acyl or an aryl group of up to 12 carbon atoms, Y is CH or N, $R^1$ for X=S or N—$R^3$ is hydrogen, a $C_1$–$C_{25}$-alkyl or $C_2$–$C_{25}$-alkene group or a phenyl radical which may be additionally substituted by one or two $C_1$–$C_4$-alkyl, $C_1$–$C_4$-alkoxy, hydroxyl, carboxyl, sulfo, amino, $C_1$–$C_4$-acylamino, nitro or cyano groups or chlorine or bromine atoms, which substituents, if there are two of them, may be identical or different, R for X=O is phenyl, o-, m- or p-tolyl, p-chlorophenyl, m-nitrophenyl, m-methoxyphenyl or m-methylsulfonylphenyl, $R^2$ for X=S or N—$R^3$ is hydrogen, a $C_1$–$C_4$-alkyl, $C_1$–$C_4$-alkoxy, hydroxyl, carboxyl, sulfo, amino or $C_1$–$C_4$-acylamino group or a chlorine or bromine atom, and $R^2$ for X=O is hydrogen, as bleach activators or optical brighteners in washing and cleaning agents.

The present invention also relates to washing and cleaning agents which contain compounds I.

In EP-B 099 197 (1) and EP-B 240 057 (2) customary bleach activators mentioned for washing and cleaning agents include acylated amines such as tetraacetylethylenediamine (TAED), acylated sugars such as pentaacetylglucose, carboxylic esters such as sodium p-acetoxybenzenesulfonate and a number of acylated heterocyclic compounds, namely hydantoins, cyclic hydrazides, triazoles, urazoles, imidazolines, glycolurils, piperazines and cyclic ureas.

U.S. application No. 3 822 114 (3) describes aldehyde and ketone compounds for use as bleach activators. The examples mentioned therein of heterocyclic ketones include piperidine derivatives and also tetrahydrothiopyranone and 4-oxacyclohexanone derivatives.

J. Org. Chem. 14 (1949), 967–81, (4), describes the preparation of benz-(4H)1,3-oxazin-4-one and 2-substituted derivatives. The substituents mentioned are methyl, ethyl, n-propyl, phenyl, o- and p-tolyl, o- and p-chlorophenyl, o- and p-nitrophenyl and also 3-pyridyl. Nothing is said about application properties of these compounds.

EP-A-332 294 (5) relates to washing agent compositions which contain inter alia benz-(4H)1,3-oxazin-4-ones of the formula I (X=O, Y=CH, $R^2$=H) as bleach activators, where $R^1$ is hydrogen, alkyl, alkaryl, aryl, aralkyl, alkoxy, haloalkyl, amino, aminoalkyl, carboxyl or a carboxyl-containing group. The Description and the Examples mention without exception only compounds where $R^1$ is alkyl, in particular methyl, amino, aminoalkyl, acyl, alkoxy, haloalkyl, alkoxyalkyleneoxy or alkylenecarboxylate.

The prior art bleach activators have been found to be in need of improvement. Especially the amount needed of these agents in washing and cleaning agents to obtain an adequate effect is frequently too high.

It is an object of the present invention to provide bleach activators which if used in a smaller amount produce the same effect as the prior art agents.

We have found that this object is achieved by using for this purpose the heterocyclic compounds I mentioned at the beginning.

The compounds I to be used according to the present invention belong for the case Y=CH to the substance classes of the benz-(4H)1,3-oxazin-4-ones (X=O), benz-(4H)1,3-thiazin-4-ones (X=S) and (4H)1,3-quinazolin-4-ones (X=N—$R^3$ or to the corresponding pyridofused compounds (Y=N).

In a preferred embodiment, use is made of benz-(4H)1,3-oxazin-4-one derivatives (Y=CH) where $R^1$ is as defined for the case X=O. Particular preference is given to the use of 2-(p-tolyl)-, 2-(p-chlorophenyl)-, 2-(m-nitrophenyl)-, 2-(p-methylsulfonylphenyl)- and in particular 2-phenyl-benz-(4H)1,3-oxazin-4-one.

In a further preferred embodiment, use is made of benz-(4H)1,3-thiazin-4-one (Y=CH) and (4H)1,3-quinazo-lin-4-one (Y=CH) and also of their derivatives where $R^1$ and $R^2$ are each as defined for the case X=S or N—$R^3$.

Suitable $R^3$ is $C_1$–$C_{25}$-allcyl, preferably $C_1$–$C_{10}$-alkyl, eg. methyl, ethyl, n-propyl, n-butyl, 2-ethylhexyl or isononyl, $C_1$–$C_{25}$-acyl, preferably $C_1$–$C_{10}$-acyl, eg. formyl, acetyl, propionyl, butyryl or octanoyl, or aryl of up to 12 carbon atoms such as naphthyl, biphenyl, tolyl, xylyl or in particular phenyl.

Suitable radicals $R^1$ for the case X=S or N—$R^3$ are besides hydrogen:

$C_1$–$C_{25}$-alkyl groups, preferably $C_1$–$C_{10}$alkyl groups, which may be straight-chain or branched, for example methyl, ethyl, n-propyl, n-butyl, tert-butyl, n-pentyl, n-hexyl, n-heptyl, 1-ethylpentyl, n-octyl, 2,4,4-trimethylpentyl, n-nonyl, n-decyl, n-undecyl, n-tridecyl, n-pentadecyl and n-heptadecyl $C_2$–$C_{25}$-alkenyl groups, preferably $C_2$–$C_6$- and $C_{15}$–$C_{2-1}$alkenyl groups, for example vinyl, 1-propenyl, 2-propenyl, heptadec-8-enyl, heptadeca-8,11-dienyl and heptadeca-8,11,14-trienyl a phenyl radical which may additionally carry one or two, preferably one, substituent, for example phenyl, o-, m- or p-tolyl, 2,3-, 2,4-, 2,5-, 2,6-, 3,4- or 3,5-dimethylphenyl, o-, m- or p-ethylphenyl, m- or p-tert-butylphenyl, o-, m- or p-methoxyphenyl, 2,3-, 2,4-, 2,5-, 2,6-, 3,4- or 3,5-dimethoxyphenyl, o-, m- or p-hydroxyphenyl, 3-hydroxy-4-methoxy-phenyl, o-, m- or p-carboxyphenyl, o-, m- or p-sulfophenyl, o-, m- or p-aminophenyl, o-, m- or p-acetaminophenyl, o-, m- or p-nitrophenyl, o-, m- or p-cyanophenyl, o-, m- or p-chlorophenyl and o-, m- or p-bromophenyl.

Suitable radicals $R^2$ for the case X=S or N—$R^3$ are besides hydrogen a $C_1$–$C_4$-alkyl group, eg. methyl, ethyl, n-propyl, isopropyl, n-butyl or tert-butyl, a $C_1$–$C_4$-alkoxy group, eg. methoxy, ethoxy, n-butoxy or tert-butoxy, a hydroxyl, carboxyl, sulfo, amino or $C_1$–$C_4$-acylamino group, eg. acetamino, propionylamino or butyrylamino, and also a chlorine or bromine atom. These substituents may be in the 5-, 6-, 7- or 8-positions.

Preferred radicals R here are hydrogen, $C_1$–$C_4$-alkyl, $C_1$–$C_4$-alkoxy and hydroxyl.

The compounds I are outstandingly suitable for use as bleach activators or as optical brighteners for washing and cleaning agents, in particular in the washing of household textiles at temperatures of from 30° to 60° C. Usually, only about a third of the amount of I as bleach activator is required, compared with the customary bleach activators, in order to obtain the same effect with the former as with the latter.

The present invention further provides washing and cleaning agents which contain from 0.1 to 10% by weight, preferably from 0.5 to 6% by weight, based on the total amount of the formulation, of one or more heterocyclic compounds I.

To improve the bleach activator effect, the washing and cleaning agents may additionally contain further customary bleach activators in the amounts customary for this purpose.

Suitable additional bleach activators are in particular:

polyacylated sugars, eg. pentaacetylglucose;

acyloxybenzenesulfonic acids and their alkali metal and alkaline earth metal salts, eg. sodium p-isononanoyloxybenzenesulfonate or sodium p-benzoyloxybenzenesulfonate;

N-diacylated and N,N'-tetraacylated amines, eg. N,N,N',N'-tetraacetyl-methylenediamine and -ethylenediamine, N,N-diacetylaniline, N,N-diacetyl-p-toluidine or 1,3-diacylated hydantoins such as 1,3-diacetyl-5,5-dimethylhydantoin.

However, as additional bleach activators it is also possible to use the following:

N-alkyl-N-sulfonylcarboxamides, eg. N-methyl-N-mesylacetamide or N-methyl-N-mesylbenzamide;

N-acylated cyclic hydrazides, acylated triazoles or urazoles, eg. monoacetylmaleohydrazide;

O,N,N-trisubstituted hydroxylamines, eg. O-benzoyl-N,N-succinylhydroxylamine, O-acetyl-N,N-succinylhydroxylamine or O,N,N-triacetylhydroxylamine;

N,N'-diacylsulfurylamides, eg. N,N'-dimethyl-N,N'-diacetylsulfurylamide or N,N'-diethyl-N,N'-dipropionylsulfurylamide;

triacyl cyanurates, eg. triacetyl cyanurate or tribenzoyl cyanurate;

carboxylic anhydrides, eg. benzoic anhydride, m-chlorobenzoic anhydride or phthalic anhydride;

1,3-diacyl-4,5-diacyloxyimidazolines, eg. 1,3-diacetyl-4,5-diacetoxyimidazoline;

tetraacetylglycoluril and tetrapropionylglycoluril;

diacylated 2,5-diketopiperazines, eg. 1,4-diacetyl-2,5-diketopiperazine;

acylation products of propylenediurea and 2,2-dimethylpropylenediurea, eg. tetraacetylpropyl-enediurea;

α-acyloxypolyacylmalonamides, eg. α-acetoxy-N,N'-diacetylmalonamide;

diacyldioxohexahydro-1,3,5-triazines, eg. 1,5-diacetyl-2,4-dioxohexahydro-1,3,5-triazine.

Washing and cleaning agent formulations which contain the compounds I with or without further customary bleach activators generally contain as additional constituents, based on the total weight of the formulation, from 6 to 25% by weight of surfactants, from 15 to 50% by weight of builders and possibly co-builders, from 10 to 30% by weight of bleaching agents and from 5 to 30% by weight of auxiliaries such as enzymes, foam regulators, corrosion inhibitors, further optical brighteners, perfumes, dyes or formulation aids, eg. sodium sulfate, in the respective customary amounts. The detailed specifications of these constituents will be known to the person skilled in the art and therefore need not be further explained here.

EXAMPLES

Use of benz-(4H)1, 3-oxazin-4-ones I and bleach activators in household washing agents Washing agent formulations of the composition 6.25% by weight of sodium dodecylbenzenesulfonate
4.7% by weight of ethoxylated $C_{13}$–$C_{15}$ oxo process alcohol with 7 mol of ethylene oxide
2.8% by weight of tallow fat soap
1.0% by weight of carboxymethylcellulose
2.0% by weight of copolymer of maleic acid and acrylic acid (weight ratio 30 : 70, average molecular weight 70,000)
4.5% by weight of sodium disilicate
1.0% by weight of magnesium silicate
25.0% by weight of zeolite A
10.0% by weight of sodium perborate monohydrate
x % by weight of bleach activator (30.75-x) % by weight of sodium sulfate were investigated in respect of their suitability for washing textiles. The amount x and the nature of the bleach activator are indicated in the table.

In each case this test washing agent was used in the washing liquor in an amount of 8 g/l.

The following washing conditions were employed:

The washing machine used was the Launder-O-meter from Atlas.

The hardness of the wash water was 16.8° German hardness ≏ 3 mmol of $Ca^{2+}$/l ($Ca^{2+}$: $Mg^{2+}$ = 3 : 1)

The washing time including the heating-up time was in each case 30 minutes and the liquor ratio was 12.5 : 1.

The following test fabrics were used:

A: cotton fabric with Immedial black as test stain (test fabric EMPA 115)

B: polyester fabric with carotene/edible oil stain

In each case the degree of bleaching was determined on the basis of photometric measurement of the reflectance of the fabric before and after the wash using an Elrepho (data color) from Zeiss at a wavelength of 460 ran (barium white standard in accordance with DIN 5033).

The degree of bleaching DB is calculated using the following expression:

$$DB = \frac{C_b - C_a}{C_b - C_o} \times 100$$

where the color intensity C (=degree of soiling of the fabric) is obtained from the Kubelka-Munk expression:

$$C = \frac{(1 - R)^2}{2R}$$

where
R = reflectance (measured)
b: before washing of the stained test fabric
a: after washing of the stained test fabric
o: before staining of the fabric.

The table shows the calculated degrees of bleaching of the test fabrics, in each case after a single wash at 20° C., 38° C. or 60° C.

TABLE

Degrees of bleaching for test fabrics A and B

| Bleach activator | Amount X [% by wt.] | Degree of bleaching DB | | | | | |
|---|---|---|---|---|---|---|---|
| | | Test fabric A | | | Test fabric B | | |
| | | 20° C. | 38° C. | 60° C. | 20° C. | 38° C. | 60° C. |
| according to the invention: | | | | | | | |
| 2-phenylbenz-(4H)1,3-oxazin-4-one | 6 | 24 | 42 | 58 | 61 | 78 | 77 |
| 2-(o-tolyl)benz-(4H)1,3-oxazin-4-one | 6 | 19 | 32 | 48 | 63 | 77 | 79 |
| 2-(m-tolyl)benz-(4H)1,3-oxazin-4-one | 6 | 19 | 29 | 43 | 62 | 76 | 77 |
| 2-(p-tolyl)benz-(4H)-1,3-oxazin-4-one | 6 | 25 | 44 | 62 | 65 | 78 | 78 |
| 2-(p-chlorophenyl)benz-(4H)1,3-oxazin-4-one | 6 | 31 | 48 | 60 | 73 | 83 | 86 |
| 2-(m-nitrophenyl)benz-(4H)1,3-oxazin-4-one | 6 | 23 | 42 | 63 | 61 | 76 | 77 |
| 2-(m-methoxyphenyl)benz-(4H)1,3-oxazin-4-one | 6 | 22 | 34 | 45 | 60 | 72 | 74 |
| 2-(m-methylsulfonylphenyl)benz-(4H)1,3-oxazin-4-one | 6 | 42 | 53 | 57 | 59 | 72 | 76 |
| for comparison: | | | | | | | |
| 2-methyl-benz-(4H)1,3-oxazin-4-one* | 6 | 15 | 25 | 43 | 58 | 70 | 73 |
| tetraacetylethylenediamine (TAED) | 6 | 14 | 20 | 24 | 60 | 65 | 69 |
| no bleach activator | 0 | 8 | 13 | 19 | 61 | 62 | 69 |

*as described in EP-A 332 294 (5)

We claim:

1. A washing and cleaning composition, comprising from 0.1 to 10% by weight, based on the total amount of said composition, of one or more heterocyclic compounds selected from the group consisting of 2-phenylbenz-(4H)-1,3-oxazin-4-one, 2-(p-chlorophenyl)benz-(4H)-1,3-oxazin-4-one, and 2-(p-tolyl)benz-(4H)-1,3-oxazin-4-one.

2. The composition of claim 1, wherein said heterocyclic compound is 2-phenylbenz-(4H)-1,3-oxazin-4-one.

3. A process for washing and cleaning an article, which comprises contacting said article with a washing composition comprising an effective amount of one or more heterocyclic compounds selected from the group consisting of 2-phenylbenz-(4H)-1,3-oxazin-4-one, 2-(p-chlorophenyl)benz-(4H)-1,3,-oxazin-4-one, and 2-(p-tolyl)benz-(4H)-1,3-oxazin-4-one.

4. The process of claim 3, wherein said washing composition comprises from 0.1 to 10% by weight, based on the total amount of said washing composition, of one or more said heterocyclic compound.

5. The process of claim 3, wherein said heterocyclic compound is 2-phenylbenz-(4H)-1,3-oxazin-4-one.

* * * * *